United States Patent
Lee

(10) Patent No.: US 10,323,357 B1
(45) Date of Patent: Jun. 18, 2019

(54) FUNCTIONAL SUBSTANCE ADSORPTION DEVICE FOR FIBER

(71) Applicant: NATURON CO., LTD, Yeongju-si, Gyeongsangbuk-do (KR)

(72) Inventor: Jang Suk Lee, Yeongju-si (KR)

(73) Assignee: NATURON CO., LTD, Yeongju-si, Gyeongsang (KR)

( * ) Notice: Subject to any disclaimer, the term of this patent is extended or adjusted under 35 U.S.C. 154(b) by 56 days.

(21) Appl. No.: 15/856,969

(22) Filed: Dec. 28, 2017

(51) Int. Cl.
| | | |
|---|---|---|
| *D06M 10/04* | (2006.01) | |
| *D06M 23/06* | (2006.01) | |
| *D06M 15/17* | (2006.01) | |
| *D06M 15/71* | (2006.01) | |
| *D21H 23/20* | (2006.01) | |
| *D21H 21/36* | (2006.01) | |
| *A61L 2/238* | (2006.01) | |
| *D21H 13/24* | (2006.01) | |
| *D21H 13/26* | (2006.01) | |
| *D21H 17/00* | (2006.01) | |

(52) U.S. Cl.
CPC .............. *D21H 23/20* (2013.01); *A61L 2/238* (2013.01); *D21H 13/24* (2013.01); *D21H 13/26* (2013.01); *D21H 17/00* (2013.01); *D21H 21/36* (2013.01); *D06M 10/04* (2013.01); *D06M 15/17* (2013.01); *D06M 15/71* (2013.01); *D06M 23/06* (2013.01)

(58) Field of Classification Search
USPC ............................................ 162/265; 28/100
See application file for complete search history.

(56) References Cited

U.S. PATENT DOCUMENTS

| | | | | |
|---|---|---|---|---|
| 4,860,685 A | * | 8/1989 | Smith ................... | D21H 25/18 118/300 |
| 5,595,071 A | * | 1/1997 | Pasad ..................... | D06B 1/02 68/5 C |
| 7,021,087 B2 | * | 4/2006 | France ................... | D06F 58/203 68/142 |
| 7,059,065 B2 | * | 6/2006 | Gerlach ................. | D06F 35/00 34/381 |
| 7,146,749 B2 | * | 12/2006 | Barron .................. | D06F 35/00 34/596 |
| 9,121,000 B2 | * | 9/2015 | Burkinshaw ........... | A01N 31/16 |
| 9,416,482 B2 | * | 8/2016 | Alexander ............ | A47L 15/4463 |
| 9,493,896 B2 | * | 11/2016 | Allen ...................... | D06B 5/00 |
| 2007/0151312 A1 | * | 7/2007 | Bruce ................... | D06F 58/203 68/3 R |

(Continued)

*Primary Examiner* — Mark Halpern
(74) *Attorney, Agent, or Firm* — Egbert Law Offices, PLLC

(57) ABSTRACT

A functional substance adsorption device for fibers including: a casing having a space formed therein and an opening and closing door located on the front surface thereof; a drum rotatably disposed inside the casing and having a space formed therein to put the fibers therein and a plurality of fine through holes formed thereon; a driving part disposed on one side of the casing to rotate the drum; and a fine particle supply part comprising a fine particle supply hose communicating with the outer periphery of the casing, a vaporization tank connected to one side of the fine particle supply hose, a pneumatic ultrasound generator disposed inside the vaporization tank to vaporize an antimicrobial agent, and an air compressor for supplying pneumatic pressure to the pneumatic ultrasound generator.

7 Claims, 7 Drawing Sheets

(56) References Cited

U.S. PATENT DOCUMENTS

Figure 1:
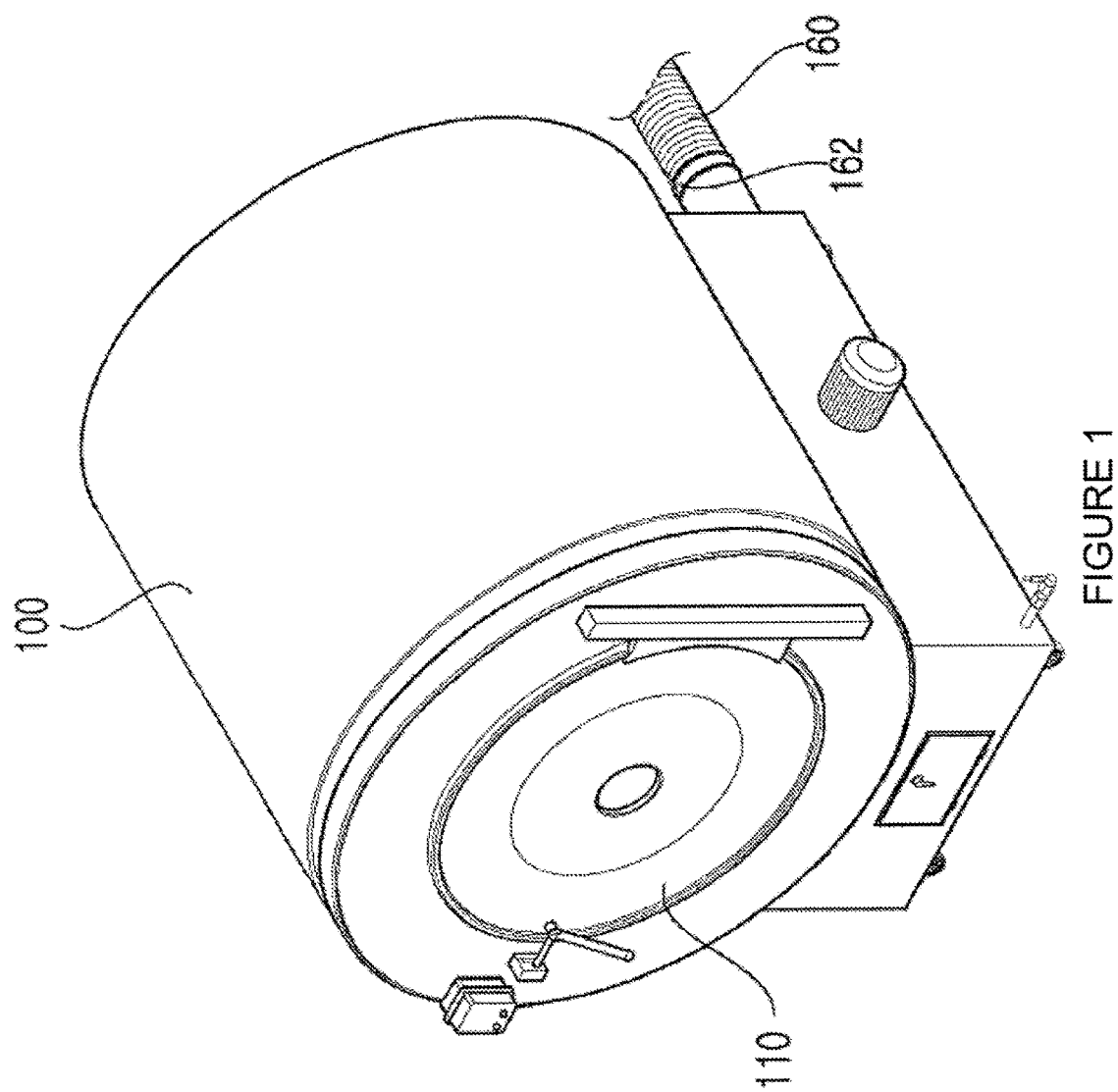

| | | | |
|---|---|---|---|
| 2007/0163094 A1* | 7/2007 | Wright | D06F 58/203 28/100 |
| 2007/0163095 A1* | 7/2007 | McAllister | D06F 58/203 28/100 |
| 2008/0176469 A1* | 7/2008 | Dong | B32B 5/26 442/58 |
| 2018/0112354 A1* | 4/2018 | Kim | D06M 15/17 |

* cited by examiner

FUNCTIONAL SUBSTANCE ADSORPTION DEVICE FOR FIBER

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to a functional substance adsorption device for fibers, and more particularly, to a functional substance adsorption device for fibers that serves to allow fine particles to adhere to the fibers, thereby improving performance of the fibers.

2. Description of Related Art Including Information Disclosed Under 37 CFR 1.97 and 37 CFR 1.98

Unless otherwise specified particularly herein, the description in the related art of the present invention does not mean prior art of the claims of the invention and is not admitted to be prior art even if included herein.

More than millions of tons of synthetic fibers have been used in many fields, and accordingly, a definite need for the improvement of antimicrobial efficiencies has been suggested continuously in fields of clothing.

So as to produce antimicrobial fibers, various organic and inorganic antimicrobial agents have been used, but as the organic antimicrobial agent has low heat resistance, it is dissolved in an extruder when mixed in a spinning process, so that it cannot be applied to fibers such as polyester and nylon.

So as to solve the above-mentioned problems, an antimicrobial silver ceramic agent produced by attaching silver compounds to porous ceramic powder has been used in production of fibers.

The sizes of ceramic particles of the antimicrobial silver ceramic agent have micron units so that the ceramic particles are substantially bulky, thereby causing the fibers to be cut during spinning and also making it impossible to be used in production of micro fibers.

Using nanotechnology, recently, many endeavors to produce antimicrobial fibers having good durability have been made. For example, silver is made to nanopowder having sizes of 100 nanometers or under, is then formed to a liquid phase, and is post-processed to fibers or is mixed directly to raw fibers during the spinning of synthetic fibers.

BRIEF SUMMARY OF THE INVENTION

Accordingly, the present invention has been made in view of the above-mentioned problems occurring in the prior art, and it is an object of the present invention to provide a functional substance adsorption device for fibers that vaporizes an antimicrobial agent or the like to the form of fine particles by means of generation of ultrasound and permeates or adsorbs the fine particles into webs of the fibers, thereby making functional fibers.

To accomplish the above-mentioned object, according to the present invention, there is provided a functional substance adsorption device for fibers including: a casing having a space formed therein and an opening and closing door located on the front surface thereof; a drum rotatably disposed inside the casing and having a space formed therein to put fibers therein and a plurality of fine through holes formed thereon; a driving part disposed on one side of the casing to rotate the drum; and a fine particle supply part for generating fine particles to supply the fine particles to the casing, the fine particle supply part comprising a fine particle supply hose communicating with the outer periphery of the casing, a vaporization tank connected to one side of the fine particle supply hose, a pneumatic ultrasound generator disposed inside the vaporization tank to vaporize an antimicrobial agent, and an air compressor for supplying pneumatic pressure to the pneumatic ultrasound generator.

BRIEF DESCRIPTION OF THE SEVERAL VIEWS OF THE DRAWINGS

The above and other objects, features and advantages of the present invention will be apparent from the following detailed description of the preferred embodiments of the invention in conjunction with the accompanying drawings, in which:

FIG. 1 is a perspective view showing a functional substance adsorption device for fibers according to the present invention.

FIG. 2 is a plan view showing the functional substance adsorption device according to the present invention.

FIG. 3 is a front sectional view showing the functional substance adsorption device according to the present invention.

FIG. 4 is a side sectional view showing the functional substance adsorption device according to the present invention.

FIG. 5 is a front sectional view showing a fine particle supply part of the functional substance adsorption device according to the present invention.

FIG. 6 is a perspective view showing a pneumatic ultrasound generator of the functional substance adsorption device according to the present invention.

FIG. 7 is a sectional view of FIG. 6.

DETAILED DESCRIPTION OF THE INVENTION

Now, an explanation on a functional substance adsorption device for fibers according to the present invention will be given with reference to the attached drawings.

An embodiment of the present invention will be in detail described so that it may be carried out easily by those having ordinary skill in the art, and therefore, this does not limit the idea and technical scope of the invention.

In the description, the sizes or shapes of the components shown in the drawing may be magnified for the clarity and convenience of the description. Further, the terms as will be discussed later are defined in accordance with the functions of the present invention, but may be varied under the intention or regulation of a user or operator. Therefore, they should be defined on the basis of the whole scope of the present invention.

Figure 2:
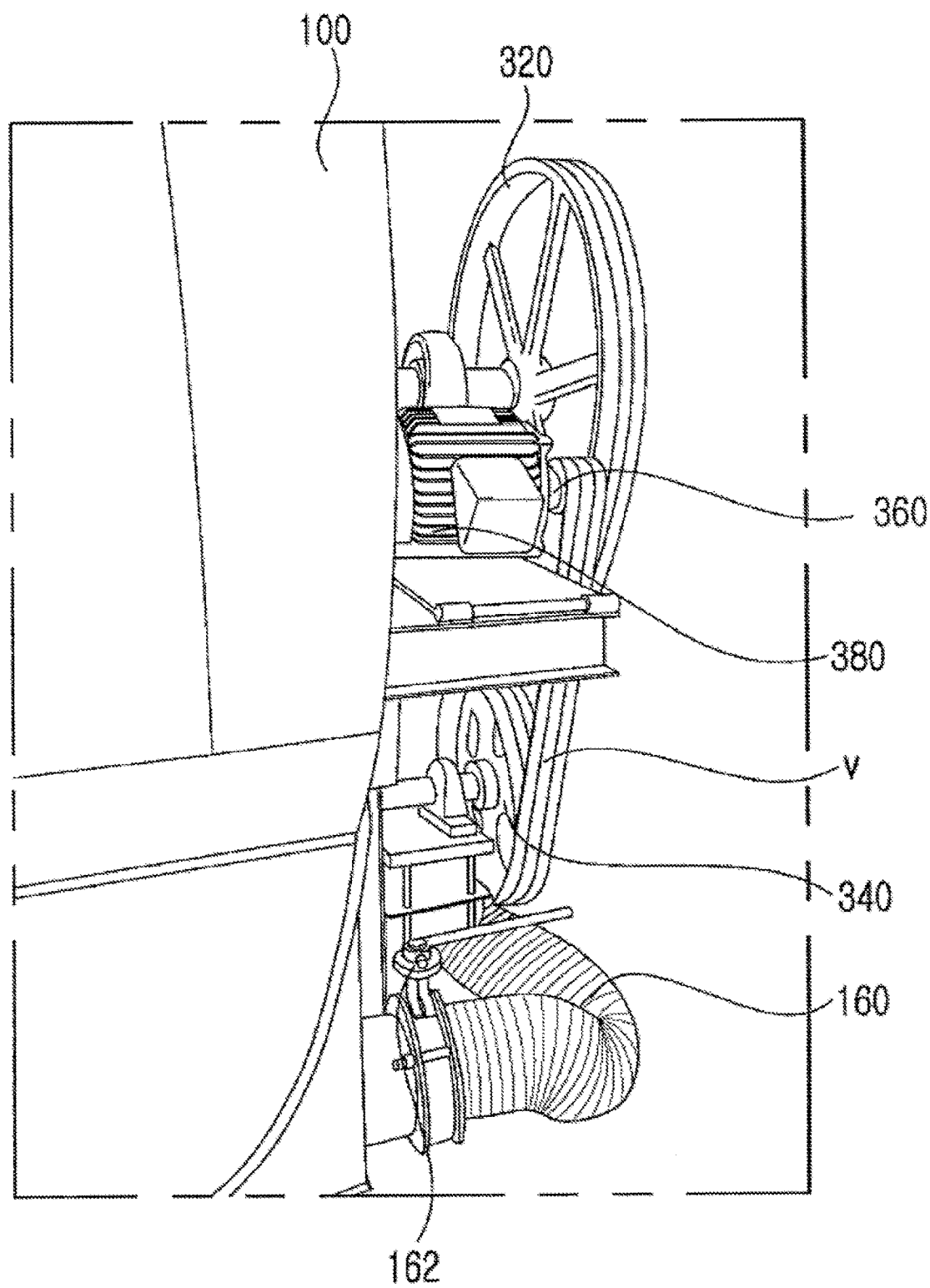
Figure 3:
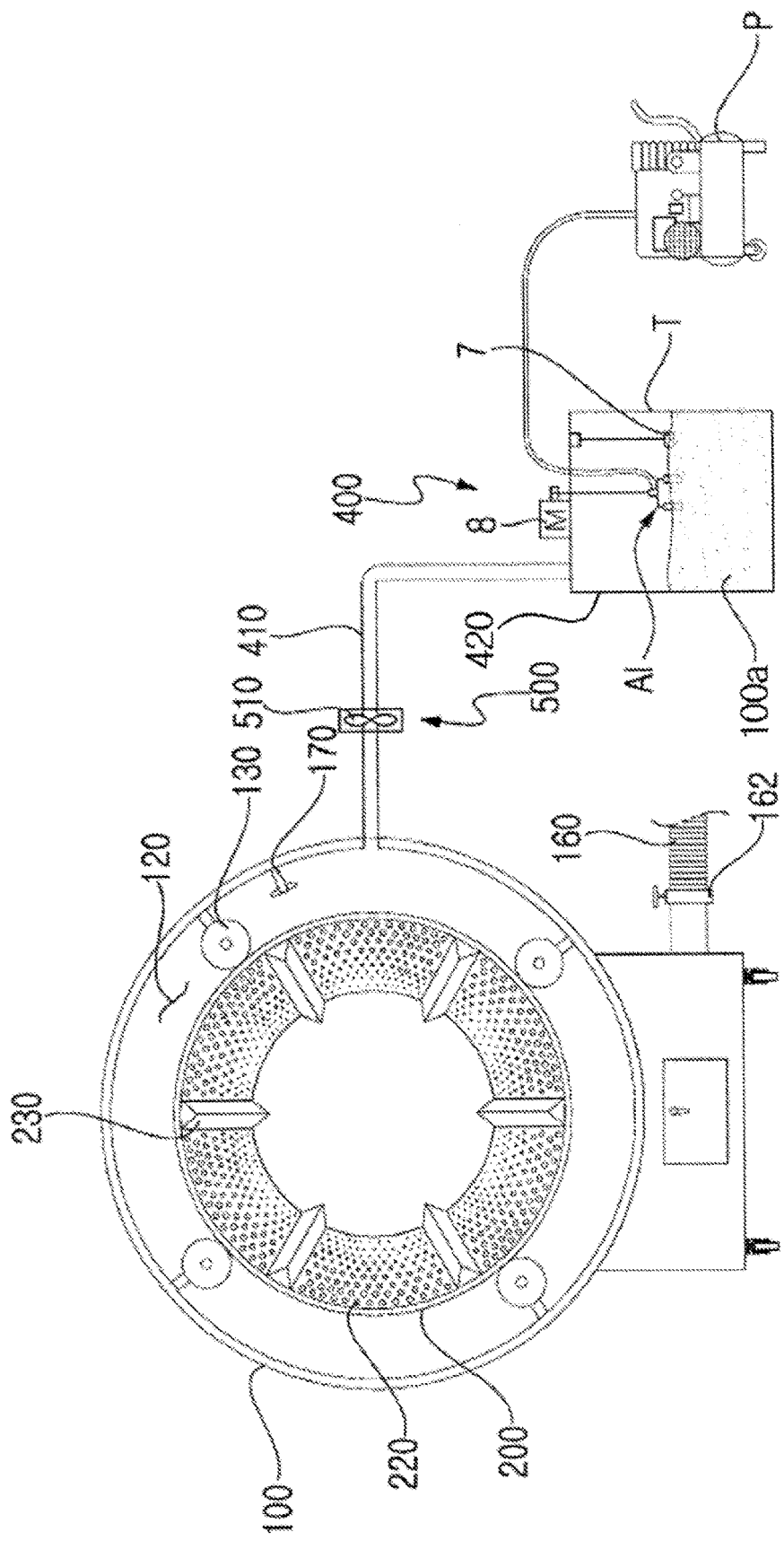
Figure 4:
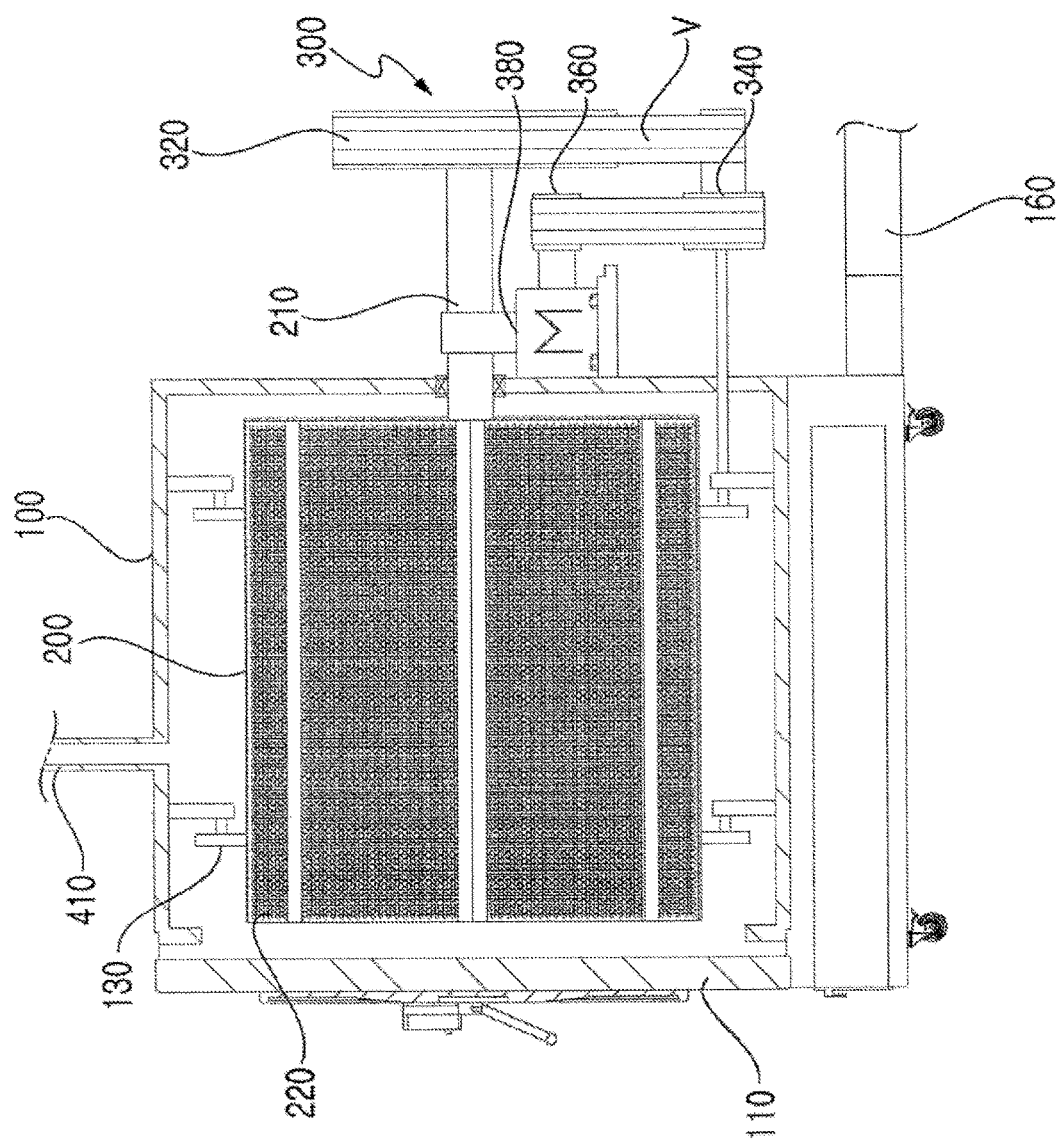
Figure 5:
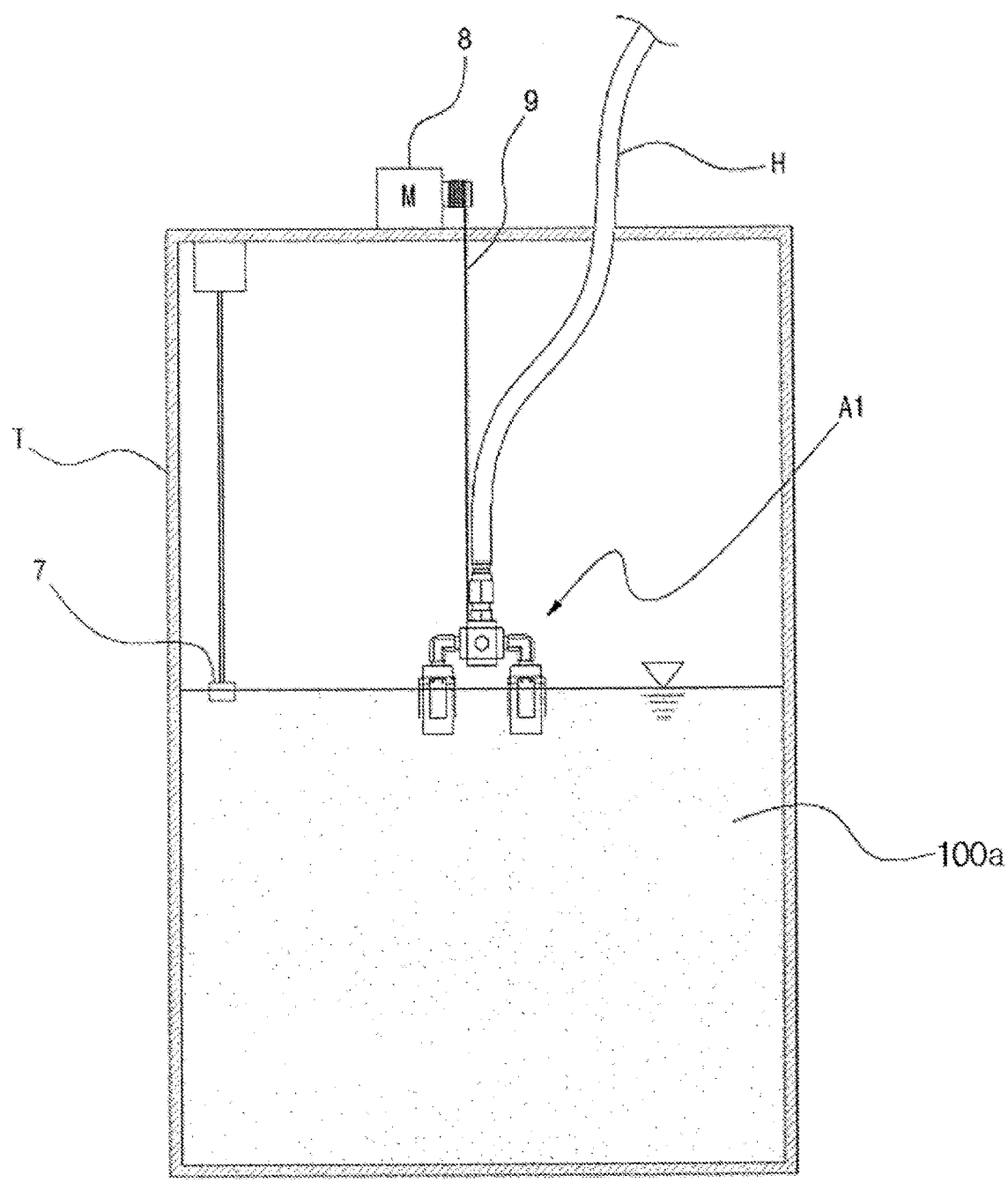
Figure 6:
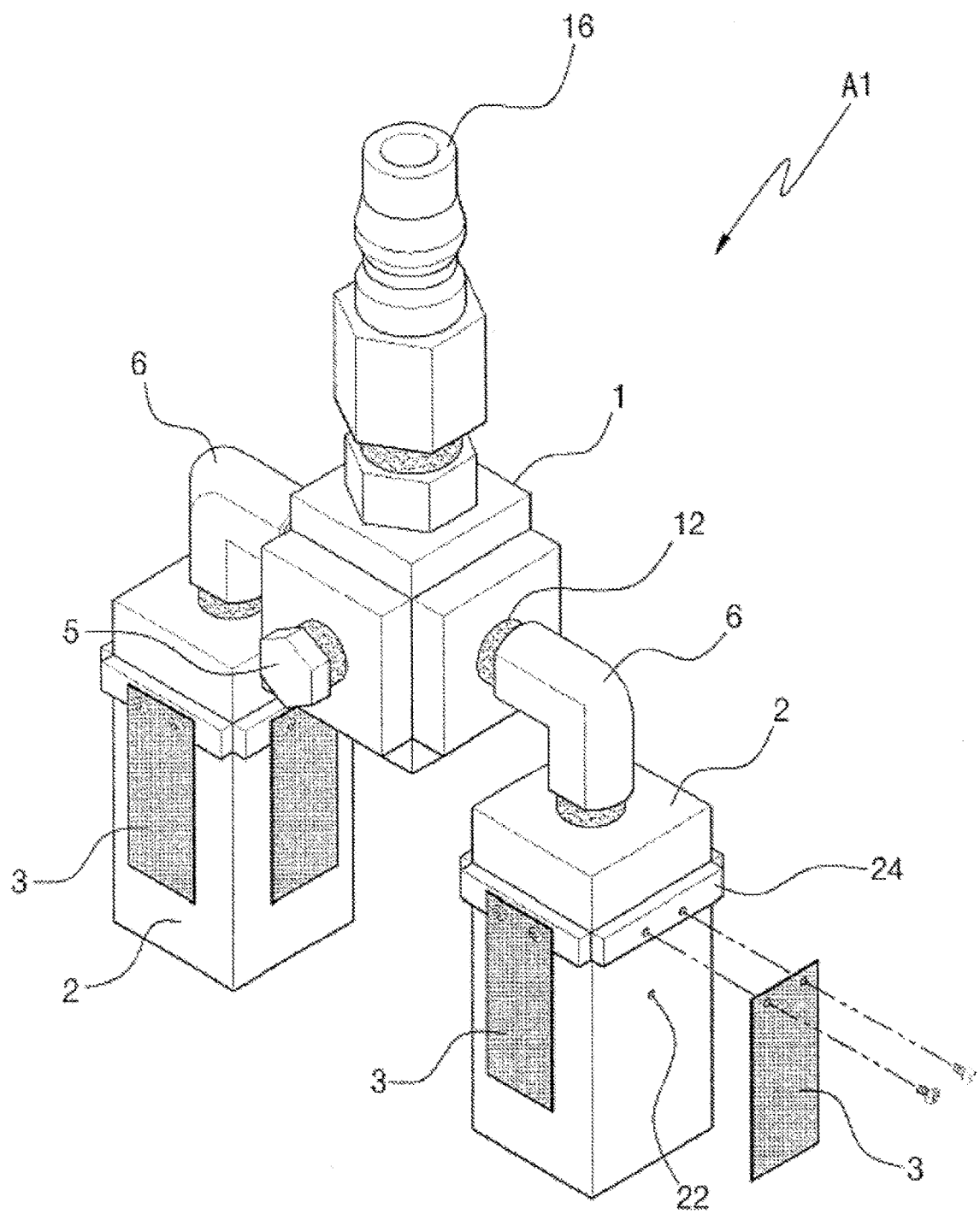
Figure 7:
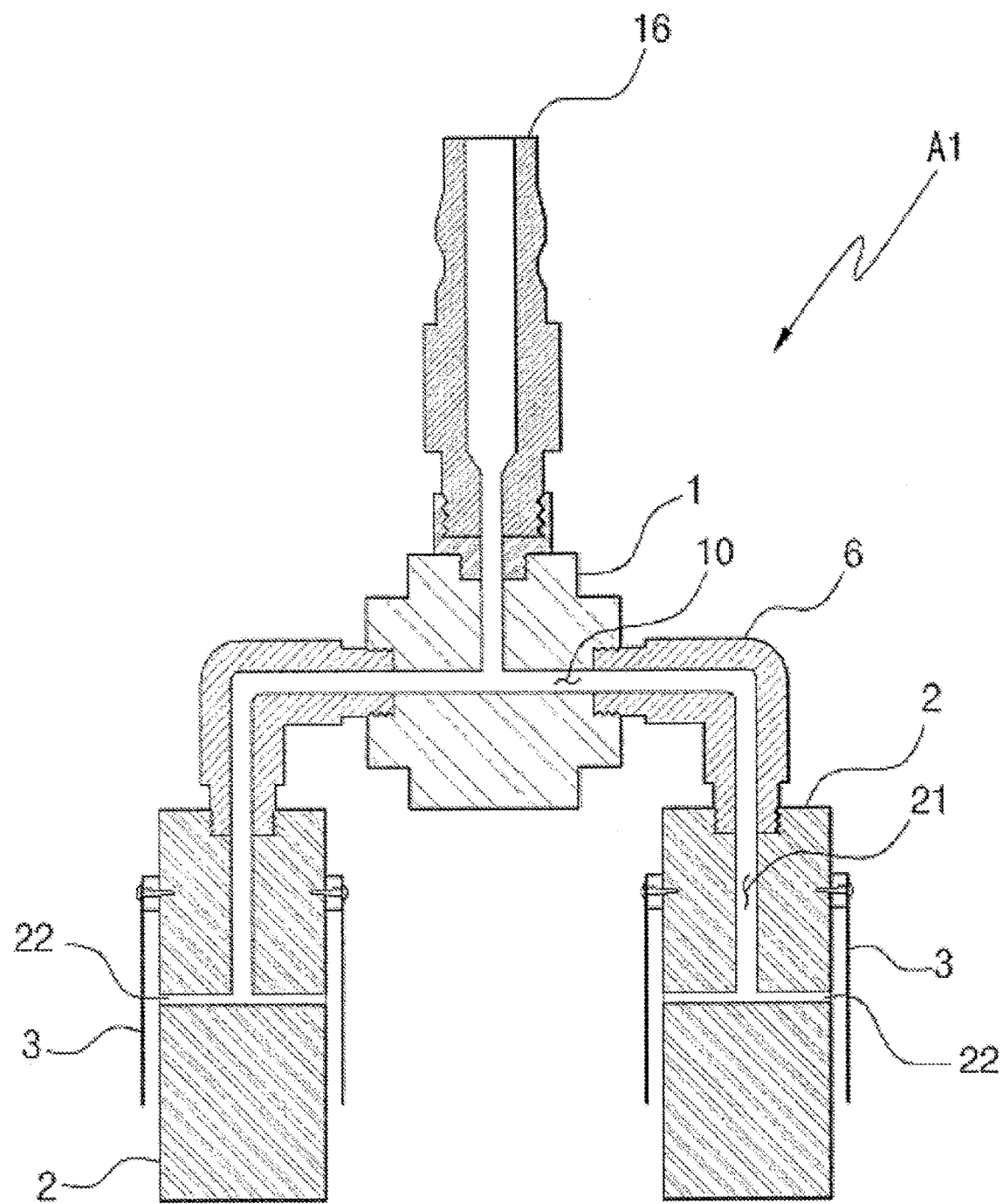

FIG. 1 is a perspective view showing a functional substance adsorption device for fibers according to the present invention, FIG. 2 is a plan view showing the functional substance adsorption device according to the present invention, FIG. 3 is a front sectional view showing the functional substance adsorption device according to the present invention, FIG. 4 is a side sectional view showing the functional substance adsorption device according to the present invention, FIG. 5 is a front sectional view showing a fine particle supply part of the functional substance adsorption device according to the present invention, FIG. 6 is a perspective view showing a pneumatic ultrasound generator of the functional substance adsorption device according to the present invention, and FIG. 7 is a sectional view of FIG. 6.

As shown in FIGS. 1 to 7, a functional substance adsorption device for fibers according to the present invention includes: a casing 100 having a space formed therein and an opening and closing door 110 located on the front surface thereof; a drum 200 rotatably disposed inside the casing 100 in such a manner as to have a space formed therein to put the fibers therein and a plurality of fine through holes 220 formed thereon; a driving part 300 disposed on one side of the casing 100 to rotate the drum 200; and a fine particle supply part 400 for generating fine particles to supply the fine particles to the casing 100, the fine particle supply part 400 comprising a fine particle supply hose 410 communicating with the outer periphery of the casing 100, a vaporization tank 420 connected to one side of the fine particle supply hose 410, a pneumatic ultrasound generator A1 disposed inside the vaporization tank 420 to vaporize an antimicrobial agent, and an air compressor P for supplying pneumatic pressure to the pneumatic ultrasound generator A1.

The casing 100 is shielded from the outside to form a chamber 120 therein.

The casing 100 includes suction means disposed on one side of the lower portion thereof in such a manner as to communicate with the chamber 120 and thus to suck the fine particles filled therein, a discharge duct 160 connected to the suction means in such a manner as to communicate with the outside, and a valve 162 mounted on the discharge duct 160 to control opening and closing of the discharge duct 160.

The suction means includes an exhaust fan disposed on an inlet side of the discharge duct 160 or a suction pump located inside the casing 100 in such a manner as to communicate with the chamber 120, and in this case, an outlet of the suction pump communicates with the discharge duct 160.

If an antimicrobial agent in form of fine particles is discharged to the air, it causes air pollution, and accordingly, a purifier is disposed on the end portion of the discharge duct 160 so as to purify the antimicrobial agent.

The purifier desirably passes the antimicrobial agent through a filter to remove the antimicrobial agent.

The chamber 120 has a plurality of agitating fans 170 disposed therein to evenly distribute and circulate the fine particles therein.

The agitating fans 170 rotate at a low speed in the chamber 120 in such a manner as to allow an air flow in the chamber 120 to be circulated. Desirably, at least one agitating fan 170 is located around an incoming hole communicating with the fine particle supply hose 410, and other agitating fans 170 are disposed to face the agitating fan 170 located around the incoming hole, so that the fine particles are evenly distributed in the chamber 120.

The drum 200 is located in the chamber 120, and a plurality of rollers 130 are disposed to come into close contact with the outer peripheral surface of the drum 200, to support the outer peripheral surface of the drum 200, and to allow the drum 200 to be kept rotating stably, so that an adsorption agent in the form of fine particles filled in the chamber 120 is permeated into the drum 200 and is then adsorbed to the fibers.

The drum 200 has a shape of a cylinder open on one side thereof and closed the other side thereof and includes the fine through holes 220 formed thereon, a rotation shaft 210, and a plurality of protruding portions 230 formed at the interior thereof.

Each protruding portion 230 is formed in a longitudinal direction of the drum 200 and has slant surfaces formed symmetrically on both sides thereof in such a manner as to have a sectional shape of '^'.

While the drum 200 is rotating, the fibers in the drum 200 are mixed by means of the protruding portions 230, and also, the binding portions of the fibers are untied, so that the adsorption agent can be evenly adsorbed to the fibers.

The driving part 300 includes the rotary shaft 210 located on the drum 200, a driven pulley 320 mounted on the rotary shaft 210, a driving pulley 340 connected to the driven pulley 320 by means of a belt V, a motor pulley 360 connected to the driving pulley 340 by means of a belt V, and a motor 380 for driving the motor pulley 360.

The pneumatic ultrasound generator A1 is connected to a height adjustment device so that it can be moved up and down according to changes in a level of antimicrobial agent.

The height adjustment device includes a level sensor 7 disposed inside the vaporization tank T to sense the level of antimicrobial agent, a motor 8 mounted on top of the vaporization tank T, and connection means 9 for connecting the motor 8 to the pneumatic ultrasound generator A1.

The level sensor 7 senses the changes in the level of antimicrobial agent.

The motor 8 includes a step motor having a rotation value limited by a set value and rotates forwardly and reversely according to signals of a controller (not shown).

The connection means 9 is a wire wound on a pulley of the motor 8, and the other end of the wire is connected to the pneumatic ultrasound generator A1. Accordingly, the wire is wound or unwound according to the rotation of the pulley in such a manner as to be adjusted in length thereof.

The level sensor 7 is connected to the controller to transmit level change data to the controller, and the controller controls the operation of the motor 8 on the basis of the level change data.

If the level of antimicrobial agent is high or low, in more detail, the motor 8 rotates forwardly or reversely to extend or reduce the length of the connection means 9 so that the pneumatic ultrasound generator A1 is moved up or down and is always kept half-submerged in the antimicrobial agent.

The pneumatic ultrasound generator A1 largely includes a main body 1, auxiliary bodies 2, and vibration plates 3.

The main body 1 has a connector 16 mounted on one side thereof in such a manner as to be connected to the air compressor P, at least one or more discharge holes 12 formed on the other side thereof, and a plurality of passages 10 formed therein in such a manner as to allow the connector 16 to communicate with the discharge holes 12.

The auxiliary bodies 12 are connected to the discharge holes 12 of the main body 1 and have passages 21 formed therein and a plurality of fine holes 22 formed on the outer surfaces thereof.

The vibration plates 3 are mounted on the auxiliary bodies 2 in such a manner as to correspond to the fine holes 22. One end of each vibration plate 3 is fixed to the corresponding auxiliary body 2, and the other end thereof is spaced apart from the outer surface of the auxiliary body 2, so that the vibration plate 3 is vibratedly operated by means of an elastic force.

The main body 1 has a shape of a hexahedron, and the discharge holes 12 are formed correspondingly on the four sides of the main body 1.

The connector 16 is located on top of the main body 1 and is thus connected to the air compressor P by means of a flexible air supply hose H.

If the auxiliary bodies 2 are connected to the respective discharge holes 12, accordingly, a minimum of one to a maximum of four auxiliary bodies are connected to the discharge holes 12. As shown in FIG. 3, two auxiliary bodies 2 are symmetrically connected to the main body 1 in a form of a straight line.

Each auxiliary body 2 has a shape of a hexahedron, and the vibration plates 3 are attached correspondingly to the four sides of the auxiliary body 2.

Each auxiliary body 2 has at least one or more fine holes 22 formed on the four sides thereof, and the fine holes 22 are formed toward the centers of the vibration plates 3.

Also, the vibration plates 3 are mounted on the auxiliary bodies 2 in a form of a cantilever so that it is vibratedly operated by means of the pressurization of compressed air discharged through the fine holes 22.

That is, one end of each vibration plate 3 is fixed to a stepped projection 24 formed on the auxiliary body 2, and the other end thereof is spaced apart from the outer surface of the auxiliary body 2, so that the vibration plate 3 is vibratedly operated by means of the elastic force.

The main body 1 is connected to each auxiliary body 2 by means of an elbow pipe 6. That is, the discharge hole 12 of the main body 1 is connected to the incoming hole of the auxiliary body 2 by means of the elbow pipe 6. Accordingly, the auxiliary bodies 2 are located under the main body 1.

Now, an explanation on the operation of the pneumatic ultrasound generator A1 of the functional substance adsorption device according to the present invention will be given below.

Compressed air or gas of 7 to 10 $Kg/m^2$ generated from the air compressor P or a high pressure gas tank is introduced into the main body 1 through the air supply hose H.

The compressed air introduced into the main body 1 is discharged to the discharge holes 12 through the passages of the main body 1 and is thus supplied to the passages 21 of the auxiliary bodies 2 through the elbow pipes 6 connected to the discharge holes 12.

After that, the compressed air supplied to the auxiliary bodies 2 passes through the fine holes 22 and collides against the vibration plates 3 to cause the vibration plates 3 to be vibrated.

In this case, one end of each vibration plate 3 is fixed to the stepped projection 24, and the other end thereof is spaced apart from the outer surface of the auxiliary body 2, so that the vibration plate 3 is vibratedly operated by means of the elastic force. In more detail, the compressed air discharged from the fine hole 22 is concentrated on a portion of the vibration plate 3 spaced apart from the auxiliary body 2, thereby allowing the portion of the vibration plate 3 to be finely vibrated at a high speed.

If the vibration plate 3 is finely vibrated at a high speed, resonant frequencies are generated to create ultrasound, and the generated ultrasound boils and vaporizes the liquid antimicrobial agent at a low (room) temperature and changes it to ultra fine particles.

The antimicrobial agent, which is changed to the form of the ultra fine particles after vaporized by means of the ultrasound, is supplied and filled in the chamber 120 of the casing 100 through the fine particle supply hose 410, is then introduced into the drum 200 through the fine through holes 220, and is finally adsorbed to webs of the fibers.

The fine particle supply hose 410 has an accelerator 500 mounted thereon to accelerate the movements of the fine particles.

The accelerator 500 has an impeller 510 located therein to move the fine particles rapidly by means of the rotation of the impeller 510.

The antimicrobial agent in the form of the ultra fine particles allows target materials from the gas or steam in a static or dynamic state to adhere to the fibers and fabrics.

Adsorption occurs when a fluid (gas or liquid droplets) is exposed to one or more unwanted or target substances (unwanted molecules) thereof at an interface with a solid and accommodates the unwanted or target substances therein or is bonded to them.

The adsorption (surface treatment) process accompanies absorption, that is, permeation of gas or liquid into a solid phase. Sorption includes the entire absorption and removal (adsorption and absorption) of gas or liquid by means of a solid material.

There is almost no physical factor capable of adsorbing the unwanted molecules under energy at a low concentration in a closed space or closed surrounding steam phase.

An adsorption theory is generally based on a Langmuir isotherm (monolayer adsorption formed on a solid surface having even energy phase), a Brunauer-Emmett-Teller (BET) theory (multilayer isotherm), a capillary condensation theory, a Polanyi adsorption potential theory (adsorption potential and adsorption characteristic curve having no influence of adsorption temperature), and a Dubinin/Radushkevich (DR) equation (adsorption under the consideration of adsorption energy).

As described above, the functional substance adsorption device according to the present invention vaporizes the antimicrobial agent or the like to the form of fine particles by means of the generation of ultrasound and permeates or adsorbs the fine particles into the webs of fibers, thereby making the functional fibers.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

I claim:

1. A functional substance adsorption device for fibers comprising:
   a casing having a space formed therein and an opening and closing door located on the front surface thereof;
   a drum rotatably disposed inside the casing and having a space formed therein to put the fibers therein and a plurality of fine through holes formed thereon;
   a driving part disposed on one side of the casing to rotate the drum; and a fine particle supply part for generating fine particles to supply the fine particles to the casing, the fine particle supply part comprising a fine particle supply hose communicating with the outer periphery of the casing, a vaporization tank connected to one side of the fine particle supply hose, a pneumatic ultrasound generator disposed inside the vaporization tank to vaporize an antimicrobial agent, and an air compressor for supplying pneumatic pressure to the pneumatic ultrasound generator.

2. The functional substance adsorption device for fibers according to claim 1, wherein the drum comprises protruding portions formed inwardly therefrom in a longitudinal direction thereof, and each protruding portion has slant surfaces formed symmetrically on both sides thereof.

3. The functional substance adsorption device for fibers according to claim 1, wherein the driving part comprises:
   a rotary shaft located on the drum;
   a driven pulley mounted on the rotary shaft;
   a driving pulley connected to the driven pulley by means of a first belt;
   a motor pulley connected to the driving pulley by means of a second belt; and
   a first motor for driving the motor pulley.

4. The functional substance adsorption device for fibers according to claim 1, wherein the pneumatic ultrasound generator comprises:
   a main body having a connector mounted on one side thereof in such a manner as to be connected to the air compressor, at least one or more discharge holes formed on the other side thereof, and a plurality of first passages formed therein in such a manner as to allow the connector to communicate with the discharge holes;
   auxiliary bodies connected to the discharge holes of the main body and having second passages formed therein and a plurality of fine holes formed on the outer surfaces thereof; and
   vibration plates mounted on the auxiliary bodies in such a manner as to correspond to the fine holes, one end of each vibration plate being fixed to the auxiliary body and the other end of each vibration plate being spaced apart from the outer surface of the auxiliary body, so that the vibration plates have elastic forces.

5. The functional substance adsorption device for fibers according to claim 4, wherein the pneumatic ultrasound generator is connected to a height adjustment device in such a manner as to be moved up and down according to changes in a level of the antimicrobial agent, and the height adjustment device comprises a level sensor disposed inside the vaporization tank to sense the level of antimicrobial agent, a second motor mounted on top of the vaporization tank, and connection means for connecting the second motor to the pneumatic ultrasound generator.

6. The functional substance adsorption device for fibers according to claim 1, further comprising an accelerator mounted on the fine particle supply hose to accelerate the movements of the fine particles.

7. The functional substance adsorption device for fibers according to claim 6, wherein the accelerator comprises an impeller located therein to move the fine particles rapidly by means of the rotation of the impeller.

* * * * *